(12) United States Patent
Mita et al.

(10) Patent No.: US 6,444,705 B2
(45) Date of Patent: Sep. 3, 2002

(54) ANGIOGENESIS INHIBITORS

(75) Inventors: Shiro Mita; Hidehito Matsuoka, both of Ikoma (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/823,360

(22) Filed: Mar. 30, 2001

Related U.S. Application Data

(63) Continuation-in-part of application No. PCT/JP99/05359, filed on Sep. 30, 1999.

(30) Foreign Application Priority Data

Oct. 2, 1998 (JP) ............................................. 10-280655

(51) Int. Cl.$^7$ ............................................. A61K 31/165
(52) U.S. Cl. ...................................... 514/618; 514/912
(58) Field of Search .................................. 514/618, 912

(56) References Cited

U.S. PATENT DOCUMENTS 5,214,181 A   5/1993   Morita et al.

FOREIGN PATENT DOCUMENTS

| JP | 10-324625 A | 12/1998 |
|---|---|---|
| WO | WO 91/08199 | 6/1991 |
| WO | WO 94/28014 | 12/1994 |

*Primary Examiner*—Zohreh Fay
(74) *Attorney, Agent, or Firm*—Frishauf, Holtz, Goodman & Chick, P.C.

(57) ABSTRACT

A method for inhibiting angiogenesis comprising administering to a patient (mammal, such as a human) in need thereof, a pharmaceutically effective amount of an angiogenesis inhibitor containing a compound of formula (I) or a pharmaceutically acceptable salt thereof, either alone or in combination with a pharmaceutically acceptable carrier. The method of treatment may be used to treat diseases in which the angiogenesis participates, particularly retinal diseases such as diabetic retinopathy, macular degeneration, retinal vein occlusion and retinal artery occlusion, neovascular glaucoma and tumors such as hemangioma.

Formula (I)

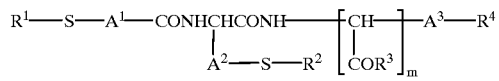

9 Claims, No Drawings

ANGIOGENESIS INHIBITORS

This application is a continuation-in-part application of International Application PCT/JP99/05359 (not published in English) filed Sep. 30, 1999.

TECHNICAL FIELD

The present invention relates to angiogenesis inhibitors containing cysteine derivatives as active ingredients and particularly provides drugs which are useful for treatment of ophthalmopathy such as retinal diseases.

BACKGROUND ART

Homeostasis of blood vessels is maintained by various functions of endothelial cells. The vascular endothelial cells have 1) an effect of mediating transportation of necessary components such as nutrition in blood to tissues and preventing unnecessarily much components from passing, 2) an effect of circulating blood smoothly without coagulation, 3) an effect of stopping bleeding when the blood vessels are transected, and 4) a regulatory effect of keeping vasotonia constant.

Angiogenesis occurs stepwise as follows; decomposition of a basement membrane by protease produced in the vascular endothelial cells, migration and proliferation of the vascular endothelial cells, lumen formation of the vascular endothelial cells, formation of the basement membrane and encirclement of peripheral cells. The angiogenesis is closely related to various diseases, particularly retinal diseases such as diabetic retinopathy, macular degeneration, retinal vein occlusion and retinal artery occlusion, neovascular glaucoma or tumors such as hemangioma.

On one hand, WO 91/08199 discloses that cysteine derivatives (general formula [I]), which are active ingredients of the present invention, are useful compounds as therapeutic agents for immunodeficiency, autoimmune diseases and the like. However, there have been no report relating to their effects of inhibiting the angiogenesis or their effects of treating retinopathy.

It is a very interesting subject to find further new pharmacological effects of these cycteine derivatives, which have been useful drugs.

DISCLOSURE OF THE INVENTION

The present inventors studied effects of cysteine derivatives on angiogenesis in order to find new pharmacological effects thereof. As a result, it was found that the cysteine derivatives had inhibitory effects on angiogenesis and were useful as therapeutic agents for diseases in which the angiogenesis participates, particularly retinal diseases such as diabetic retinopathy, macular degeneration, retinal vein occlusion and retinal artery occlusion, neovascular glaucoma and tumors such as hemangioma.

The present invention provides angiogenesis inhibitors and therapeutic agents for retinal diseases containing compounds represented by the following general formula [I] or salts thereof (hereinafter referred to as "the present compound") as active ingredients.

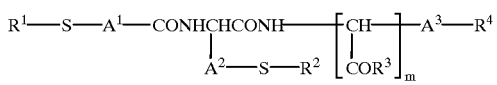

[I]

[wherein $R^1$ and $R^2$, being the same or different, are hydrogen, lower alkyl, lower alkanoyl, phenylcarbonyl, phenyl-lower alkyl or phenyl-lower alkoxycarbonyl.

$R^3$ and $R^4$, being the same or different, are hydroxy, lower alkoxy, amino or lower alkylamino.

$A^1$, $A^2$ and $A^3$, being the same or different, are straight-chain or branched lower alkylene.

"m" is 0 or 1.]

The groups defined above are described in more detail. The lower alkyl is straight-chain or branched alkyl having one to six carbon atoms such as methyl, ethyl, propyl, hexyl, isopropyl or t-butyl. The lower alkanoyl is straight-chain or branched alkanoyl having two to six carbon atoms such as acetyl, propionyl, hexanoyl, isopropionyl or t-butanoyl. The lower alkoxy is straight-chain or branched alkoxy having one to six carbon atoms such as methoxy, ethoxy, propoxy, hexyloxy, isopropoxy or t-butoxy. Examples of particularly preferred compounds are $N^1$-(6-aminohexyl)-$N^2$-(2,2-dimethyl-3-mercaptopropionyl)-L-cysteinamide represented by the following formula [II] or salts thereof.

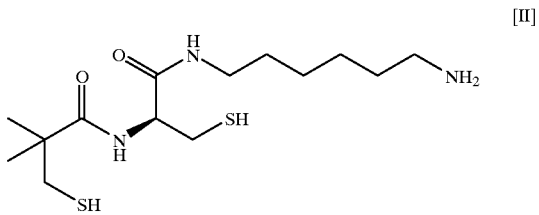

[II]

The above-mentioned salts can be pharmaceutically acceptable salts with organic or inorganic acids or bases, and examples of such salts are hydrochlorides, hydrobromides, sulfates, phosphates, lactates, maleates, fumarates, oxalates, methanesulfonates, p-toluenesulfonates, sodium salts, potassium salts, calcium salts, magnesium salts, zinc salts, ammonium salts, triethanolamine salts, dicyclohexylamine salts and the like.

There are optical isomers and diastereomers in the present compound, and drugs containing these isomers or diastereomers as active ingredients are also included in the present invention. The present compound can take the form of a solvate such as a hydrate.

In order to study utility of the cysteine derivatives represented by the general formula [I], the inhibitory effect of the present compound on angiogenesis was examined. Details will be described in the part of the pharmacological test later. It was found that the present compound had an excellent inhibitory effect on angiogenesis of a chick chorioallantonic membrane, which is an in vivo angiogenesis evaluation model. From this result, the present compound is expected to be useful as the therapeutic agents for the diseases in which the angiogenesis participates, particularly the retinal diseases such as diabetic retinopathy, macular degeneration, retinal vein occlusion and retinal artery occlusion, neovascular glaucoma and the tumors such as hemangioma.

The present compound can be administered orally or parenterally. Examples of dosage form are tablets, capsules, powders, granules, percutaneous absorbents, injections, eyedrops, eye ointments and the like. The present compound can be formulated into preparations with a pharmacutical carrier using conventional techniques. For example, oral preparations such as tablets, capsules, granules and powders can be produced by adding optionally diluents such as lactose, crystalline cellulose, starch and vegetable oil; lubricants such as magnesium stearate and talc; binders such as hydroxypropylcellulose and polyvinyl pyrrolidone; disintegrator such as calcium carboxymethylcellulose or low-substituted hydroxypropylmethylcellulose; coating agent such as hydroxypropylmethylcellulose, macrogol or silicone resin; or film forming agent such as gelatin film. Eyedrops can be produced by adding isotonic agents such as sodium chloride and concentrated glycerine; buffers such as sodium phosphate and sodium acetate; surfactants such as polyoxyethylenesorbitan monooleate, polyoxyl 40 stearate and polyoxyethylene hydrogenated castor oil; stabilizers such as sodium citrate and disodium edetate; preservatives such as benzalkonium chloride and paraben; and the like. pH can be in a range acceptable for ophthalmic preparations, and it is more preferably in a range of 4 to 8.

The dosage of the present compound can be selected suitably according to the symptoms and age of the patient (e.g. human) and dosage form and the like. In case of the oral preparation, the present compound can be administered once to several times per day with a daily dose of 0.1 to 5000 mg, preferably 1 to 1000 mg.

Results of the pharmacological test are shown below, and they are intended for better understanding the present invention but are not to limit the scope of the present invention.

BEST MODE FOR CARRYING OUT THE INVENTION

1. Inhibitory effect of the present compound on angiogenesis in the chick chorioallantoic membrane It was reported that effects of drugs on angiogenesis were evaluated using fertilized egg embryo chorioallantoic membrane as an in vivo angiogenesis evaluation model (Biochem. Biophys. Res. Commun., 174, 1070–1076 (1991)). Accordingly, effects of a cysteine derivative on the angiogenesis evaluation model were studied according to the assay described in the above-mentioned literature.

Preparation of pellet for administration

1. Methyl cellulose (0.1 g) is dissolved in sterile purified water (10 ml) to prepare a 1% solution of methyl cellulose.

2. A test compound is dissolved in ethanol/sterile purified water (1/1) to prepare a 24 μmol/ml solution.

3. The 24 μmol/ml solution of the test compound is diluted with ethanol/sterile purified water (1/1) to prepare 12 μmol/ml and 6 μmol/ml solutions of the test compound.

4. The solution (0.20 ml) of the test compound having each concentration is mixed with the 1% solution (0.20 ml) of methyl cellulose to prepare a mixed solution of the test compound.

5. The mixed solution (10 μl) of the test compound having each concentration is air-dried on a paraffin film having a diameter of 3 mm for about two hours to produce a test compound pellet.

Experimental method

Hatched eggs (white leghorn) of three days old after fertilization were put up by threes on a culture plate having six wells with their air phases upward and incubated in a $CO_2$ incubator for 20 minutes (temperature: 37° C., humidity: 95%, $CO_2$ concentration: 5%). The hatched eggs were transferred from the $CO_2$ incubator to a clean bench, and an opening of about 2 cm square was made in an eggshell in an upper portion of the air phase of the hatched egg in the clean bench. A shell membrane was peeled from a vitelline membrane, the opening in the eggshell was covered with a culture Schale, and the hatched egg was cultured in the $CO_2$ incubator for one day. The test compound pellet was placed on an embryo chorioallantoic membrane, where existing blood-vessels are few, of the hatched egg so that the pellet sticks to the embryo chorioallantoic membrane. This hatched egg was cultured in the $CO_2$ incubator for two days. Then. about 2 ml of 10% intralipid (angiographic agent) was injected into the embryo chorioallantoic membrane, and blood-vessel formation around the pellet was observed with a stereomicroscope (×10). Hatched eggs in which angiogenesis was not observed were defined as positive, and inhibition rates of angiogenesis were calculated by the following equation.

Inhibition rate of angiogenesis (%) =[(Number of hatched eggs exhibiting positive)/(Number of tested hatched eggs)]×100

Results

Table 1 shows experimental results using $N^1$-(6-aminohexyl)-$N^2$-(2,2-dimethyl-3-mercaptopropionyl)-L-cysteinamide hydrochloride as the test compound.

TABLE 1

| Dose (μmol/egg) | Inhibition rate of angiogenesis (%) |
|---|---|
| 0.00 | 0 |
| 0.06 | 80 |
| 0.12 | 93 |

As shown in Table 1, the present compound inhibited the angiogenesis remarkably though its dose was low.

The above-mentioned results of the pharmacological test clearly show that the present compound exhibits the excellent inhibitory effect on the angiogenesis and is expected to be useful as a therapeutic agent for diseases in which the angiogenesis participates, particularly retinal diseases such as diabetic retinopathy, macular degeneration, retinal vein occlusion and retinal artery occlusion, neovascular glaucoma and tumors such as hemangioma.

The present invention relates to angiogenesis inhibitors containing cysteine derivatives as active ingredients and particularly provides drugs which are useful for treatment of retinal diseases such as diabetic retinopathy, macular degeneration, retinal vein occlusion and retinal artery occlusion, neovascular glaucoma and tumors such as hemangioma.

The present invention thus relates to and provides a method for inhibiting angiogenesis comprising administering to a patient (mammal, such as human) in need thereof, a pharmaceutically effective amount of an angiogenesis inhibitor containing a compound represented by the above formula (I) or a pharmaceutically acceptable salt thereof, either alone or in combination with a pharmaceutically acceptable carrier.

The present invention also provides a method for treating retinal disease comprising administering to a patient (mammal, such as a human) in need thereof, a pharmaceutically effective amount of a compound represented by the above formula (I) or a pharmaceutically acceptable salt thereof, either alone or in combination with a pharmaceutically acceptable carrier.

What is claimed is:

1. A method for treating retinal disease comprising administering to a patient in need thereof a pharmaceutically effective amount of a compound represented by the following formula (I) or a pharmaceutically acceptable salt thereof, either alone or in combination with a pharmaceutically acceptable carrier,

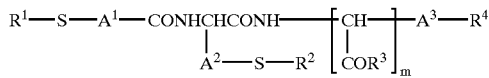
(I)

wherein $R^1$ and $R^2$ are the same or different, and are hydrogen, lower alkyl, lower alkanoyl, phenylcarbonyl, phenyl-lower alkyl or phenyl-lower alkoxycarbonyl;

$R^3$ and $R^4$ are the same or different, and are hydroxy, lower alkoxy, amino or lower alkylamino;

$A^1$, $A^2$ and $A^3$ are the same or different, and are straight-chain or branched lower alkylene; and m is 0 or 1.

2. The method as claimed in claim 1, wherein the patient is a human.

3. The method as claimed in claim 2, wherein the retinal disease is selected from the group consisting of diabetic retinopathy, macular degeneration, retinal vein occlusion, retinal artery occlusion, neovascular glaucoma and hemangioma.

4. The method as claimed in claim 2, wherein the compound is $N^1$-(6-aminohexyl)-$N^2$-(2,2-dimethyl-3-mercaptopropionyl)-L-cysteinamide.

5. The method as claimed in claim 3, wherein the compound is $N^1$-(6-aminohexyl)-$N^2$-(2,2-dimethyl-3-mercaptopropionyl)-L-cysteinamide.

6. The method as claimed in claim 1, wherein the retinal disease is intraocular angiogenesis.

7. The method as claimed in claim 2, wherein the retinal disease is intraocular angiogenesis.

8. The method as claimed in claim 6, wherein the compound is $N^1$-(6-aminohexyl)-$N^2$-(2,2-dimethyl-3-mercaptopropionyl)-L-cysteinamide.

9. The method as claimed in claim 7, wherein the compound is $N^1$-(6-aminohexyl)-$N^2$-(2,2-dimethyl-3-mercaptopropionyl)-L-cysteinamide.

* * * * *